United States Patent
Biehl et al.

(10) Patent No.: US 10,441,388 B2
(45) Date of Patent: Oct. 15, 2019

(54) DEVICE FOR DETERMINING A SUITABLE ANGULATION OF AN ABUTMENT FOR A DENTAL IMPLANT, AND ARRANGEMENT COMPRISING SUCH A DEVICE

(71) Applicant: Dentsply Implants Manufacturing GmbH, Mannheim (DE)

(72) Inventors: Volker Biehl, Neunkirchen (DE); Thomas Lange, Langenselbold (DE); Michael Aflenzer-Weisang, Mannheim (DE)

(73) Assignee: Dentsply Implants Manufacturing GmbH, Hanau (DE)

( * ) Notice: Subject to any disclaimer, the term of this patent is extended or adjusted under 35 U.S.C. 154(b) by 0 days.

(21) Appl. No.: 15/753,329

(22) PCT Filed: Jul. 14, 2016

(86) PCT No.: PCT/EP2016/001228
§ 371 (c)(1),
(2) Date: Feb. 18, 2018

(87) PCT Pub. No.: WO2017/028938
PCT Pub. Date: Feb. 23, 2017

(65) Prior Publication Data
US 2018/0235735 A1    Aug. 23, 2018

(30) Foreign Application Priority Data

Aug. 19, 2015 (DE) .......... 10 2015 113 703

(51) Int. Cl.
*A61C 8/00* (2006.01)
*A61C 19/04* (2006.01)

(52) U.S. Cl.
CPC .......... *A61C 8/009* (2013.01); *A61C 8/0053* (2013.01); *A61C 19/04* (2013.01)

(58) Field of Classification Search
CPC ........ A61C 8/009; A61C 8/0053; A61C 19/04
(Continued)

(56) References Cited

U.S. PATENT DOCUMENTS 4,932,868 A * 6/1990 Linkow ............... A61C 8/0018
433/174
5,800,168 A * 9/1998 Cascione ............. A61C 1/084
433/75
(Continued)

FOREIGN PATENT DOCUMENTS

DE    29817955 U1 * 12/1998 .......... A61C 8/0089
DE    29817955 U1    12/1998
(Continued)

OTHER PUBLICATIONS

Hartmann et al., Machine translation of specifition of DE 29817955 U1, date Dec. 1998.*
(Continued)

*Primary Examiner* — Heidi M Eide
*Assistant Examiner* — Mirayda A Aponte
(74) *Attorney, Agent, or Firm* — Katterle Nupp LLC; Paul Katterle

(57) ABSTRACT

A device is provided for determining the angulation of an abutment for a dental implant. The device includes a conical projection extending from a housing. The conical projection is adapted for insertion into a hole in the dental implant. A rotary body is disposed in the housing and is rotatable among a plurality of different angular positions relative to the conical projection. A rod-shaped indicator is connected to the rotary body. The rotary body can be secured to the housing in one of the angular positions by a locking device. The device may be part of an assembly that includes an indicator device having a receiving opening for accommodating the conical projection and an indicator scale that
(Continued)

includes a plurality of marked sectors corresponding to a plurality of predefined abutments, respectively. The location of the rod-shaped indicator relative to the marked sectors indicates the predefined abutment that should be selected.

19 Claims, 8 Drawing Sheets

(58) Field of Classification Search
 USPC .......................................................... 433/75
 See application file for complete search history.

(56) References Cited

U.S. PATENT DOCUMENTS

| | | | |
|---|---|---|---|
| 5,876,204 A * | 3/1999 | Day ........................ | A61C 1/084 433/173 |
| 8,434,337 B2 * | 5/2013 | Meitner ................. | A61C 9/002 33/412 |
| 9,072,575 B1 | 7/2015 | Alotaibi | |
| 9,320,577 B1 * | 4/2016 | Alotaibi ................ | A61C 8/0074 |
| 2015/0173863 A1 * | 6/2015 | Mittelstadt ........... | A61C 8/0053 433/201.1 |

FOREIGN PATENT DOCUMENTS

| | | | | |
|---|---|---|---|---|
| JP | 3637978 | | 4/2005 | |
| JP | 3637978 B2 * | | 4/2005 | ........... A61C 8/0089 |

OTHER PUBLICATIONS

Maikeru et al., Machine translation of specification of JP 3637978 B2 (Description JPH08252269), date Apr. 2005.*
English Translation of Written Opinion of the International Search Authority for WO2017028938.
English Translation of International Search Report for WO2017028938.

* cited by examiner

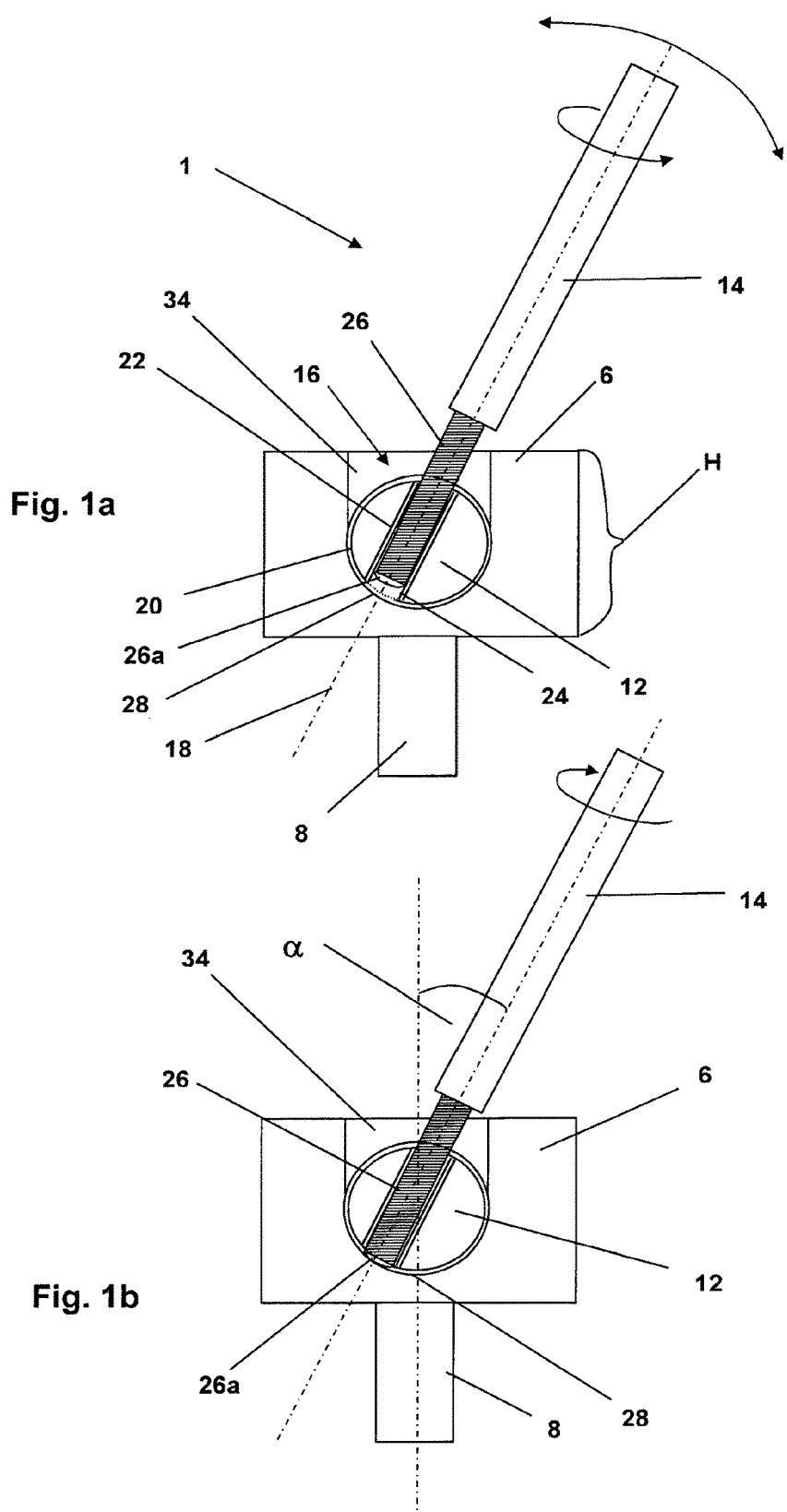

DEVICE FOR DETERMINING A SUITABLE ANGULATION OF AN ABUTMENT FOR A DENTAL IMPLANT, AND ARRANGEMENT COMPRISING SUCH A DEVICE

CROSS-REFERENCE TO RELATED APPLICATION(S)

This application is the U.S. national phase of PCT Application No. PCT/EP2016/001228 filed on Jul. 14, 2016, which claims priority to German Patent Application No. 10 2015 113 703.8 filed on Aug. 19, 2015, the disclosures of which are incorporated in their entirety by reference herein.

TECHNICAL FIELD

The present disclosure relates to a device for determining the suitable angulation of an abutment to be inserted into an implanted dental implant, and an assembly including such a device for selecting an angled abutment for a dental implant from a plurality of predefined abutments having different angulations.

BACKGROUND

For implanting artificial teeth into a jaw bone, two-piece dental implants are increasingly used, which include an implant body screwable into the jaw bone and an abutment insertable into the implant body and connectable to the implant body, to which the dental prosthesis generally referred to as superstructure, for example a crown or a removable prosthesis, is fastened.

After inserting the implant body into the jaw bone, in order to align the angle between the longitudinal axis of the implant body and the longitudinal axis of the abutment protruding from the implant body in such a manner that the abutment points substantially into the same direction as the axis of the adjacent teeth or dental implants, it is known to insert abutments at different angles, which in the art are also referred to as angulations.

Since it is moreover required for the optimal adaptation of the superstructure to also consider the type of the abutment and the height of the gingiva when selecting a suitable abutment, so that subsequently an optimal fitting accuracy of the dental prosthesis results, manufacturers in practice provide a plurality of possible abutment variations for a dental implant, from which the dentist or the dental laboratory has to select the most suitable variation so as to obtain a satisfactory outcome at the end of a treatment.

In this way, the applicant for example distributes implant systems under the designation "Ankylos", in which in total five different types of abutments, having respectively four different gingival heights and combined have six different angulations for each abutment type and gingival height, are used. This results in a total of approximately 120 different variations of abutments, from which the dentist after inserting the implant body must select the most suitable variation.

In order to prevent, for cost reasons, that a respective quantity of applicable real abutments must be stocked when selecting a suitable variation in practice trial abutments are conventionally used, which are for example manufactured from plastic material and are stored in a storage container having, for example, 120 individual compartments similar to a display case. In this instance, the dentist must be very experienced to select the suitable variation from the plurality of trial abutments in a targeted manner. Within this context, a further problem results from keeping the trial abutments in the storage container sterile or to again sterilize the trial abutments after the trial insertion into an implant body and to introduce the trial abutments into the respective compartment of the storage container.

SUMMARY

Accordingly, the disclosure describes an assembly for selecting one of a plurality of predefined abutments having different angulation angles. The assembly includes a device by which the angulation of an abutment to be inserted into an implanted dental implant can be determined with little effort. The device includes a housing and a projection fastened to the outside of the housing. The projection is insertable into an internal hole of the dental implant. A rotary body is rotatably disposed in the housing relative to the projection. A rod-shaped indicator is connected to the rotary body and a locking device is provided for releasably coupling the rotary body to the housing. The rotary body is rotatable to allow the rod-shaped indicator to pivot among a plurality of different angular positions relative to the projection, wherein each angular position of the rod-shaped indicator is determined by the angle between a longitudinal axis of the rod-shaped indicator and a longitudinal axis of the projection. The rod-shaped indicator may be locked in any one of the angular positions by the locking device coupling the rotary body to the housing.

The assembly further includes an indicator device, which includes a receiving opening for accommodating the projection of the device. The receiving opening has a longitudinal axis. A display scale is disposed laterally from the receiving opening and extends in a plane disposed parallel to the longitudinal axis of the receiving opening. An angle between the longitudinal axis of the receiving opening and the longitudinal axis of the rod-shaped indicator can be read from the display scale. The angle read from the display scale may be used to select the one of the predefined abutments. In this regard, the display scale may include a plurality of marked sectors corresponding to the predefined abutments, respectively. The location of the rod-shaped indicator relative to the marked sectors indicates the predefined abutment that should be selected.

BRIEF DESCRIPTION OF THE DRAWING

The features, aspects, and advantages of the present disclosure will become better understood with regard to the following description, appended claims, and accompanying drawings where:

FIG. 1a shows schematically a lateral cross-sectional view of the device according to the present disclosure in the released position;

FIG. 1b shows schematically a lateral cross-sectional view of the device according to the present disclosure in the locked position;

DETAILED DESCRIPTION OF ILLUSTRATIVE EMBODIMENTS

Figure 2A:
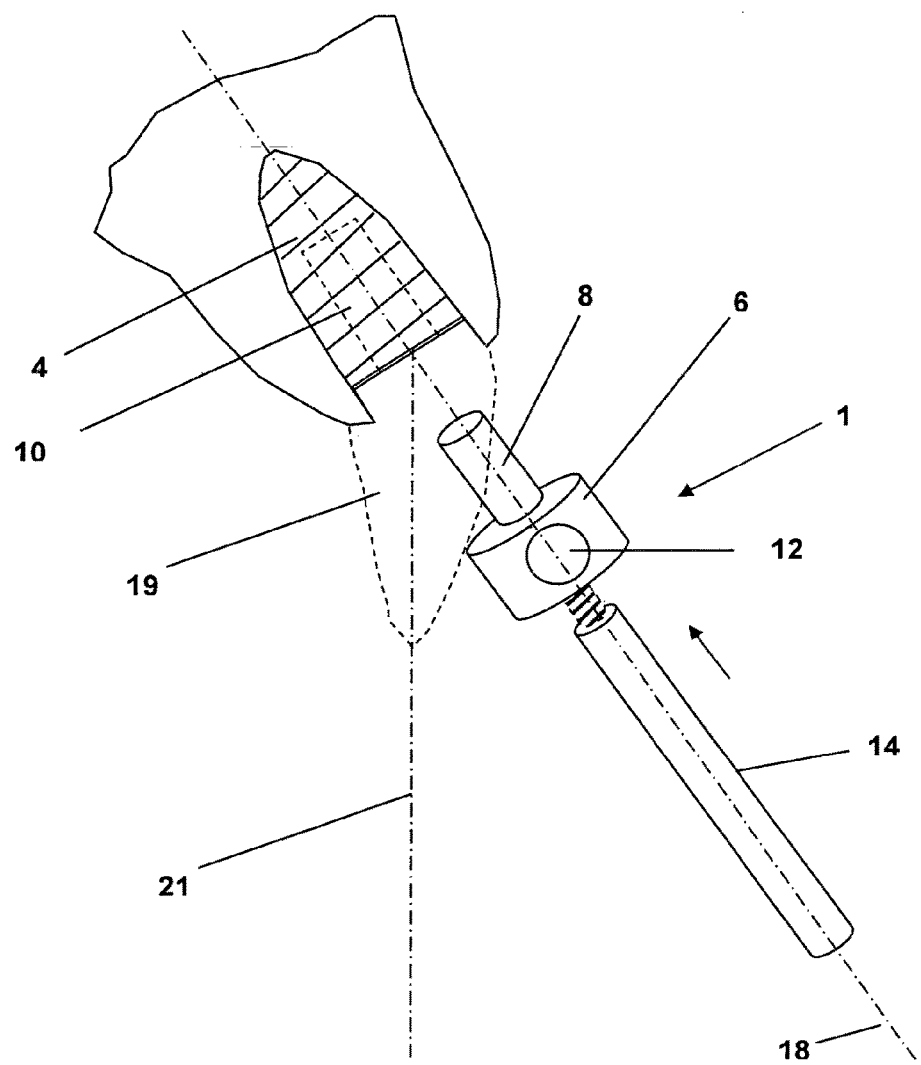
FIG. 2a shows schematically a cross-sectional view of a jaw bone having an implanted dental implant before insertion of the device according to the present disclosure into the internal hole of the dental implant.

According to the present disclosure, a device for determining the angulation of an abutment, which is to be inserted into a dental implant previously implanted, includes a housing, at the outside of which a conical projection is fastened. The conical projection, which, for example, has a parallel walled, conical or hexagonal or any other shape, is inserted into the internal hole of the implant body, subsequently referred to as dental implant, preferably having little play. The device includes furthermore a rotary body, which in the housing is accommodated in a rotary manner relative to the conical projection, and a rod-shaped indicator connected to the rotary body. In this instance, the rod-shaped indicator preferably extends radially away from the surface shell of the rotary body, which preferably is configured as a cylindrical or cylinder shaped rotary body.

The device according to the present disclosure is characterized by the fact that the rotary body is in different rotational angle positions coupleable in a rotationally fixed manner to the housing by a locking device acting between the rotary body and the housing.

It advantageously results from the present disclosure that the dentist, after inserting the conical projection into the internal hole of the already implanted dental implant, can manually move the rod-shaped indicator after releasing the locking device into such a position, in which the longitudinal axis of the rod-shaped indicator is substantially parallel to the longitudinal axis of the adjacent teeth and/or the adjacent superstructures and/or to an alignment desirable for restoring the chewing function of a future provision, that is a prosthesis for an edentulous jaw. After the alignment, the dentist actuates the locking device, as a result of which the rod-shaped indicator in the selected rotational angle position is coupled in a rotationally fixed manner to the housing so that a fixed angle results between the longitudinal axis of the conical projection and the longitudinal axis of the rod-shaped indicator element, which corresponds to the ideal angulation angle of the abutment to be inserted.

After removing the device using the locked rotation angle between the rod-shaped indicator and the conical projection, the dentist can then on the basis of the angle select a respective, most suitable abutment from the plurality of potential abutments, which he inserts into the implant body and, for example, fixes to the implant body in a known manner by screwing or using adhesive bonding to subsequently attach the superstructure to the abutment.

The present disclosure has the advantage that, by knowing the optimal angulation angle, the quantity of device variations, which the dentist must insert on a trial basis into an implanted implant body for ascertaining a suitable abutment, is significantly reduced. As a result, the task of the dentist is primarily reduced to first determine the suitable abutment type and the fitting gingival height, which, for example, may be carried out by a trial insertion of differently designed devices according to the present disclosure. If a device having a suitable shape and gingival height has been determined by a trial insertion, the suitable angulation is subsequently determined.

Figure 2B:
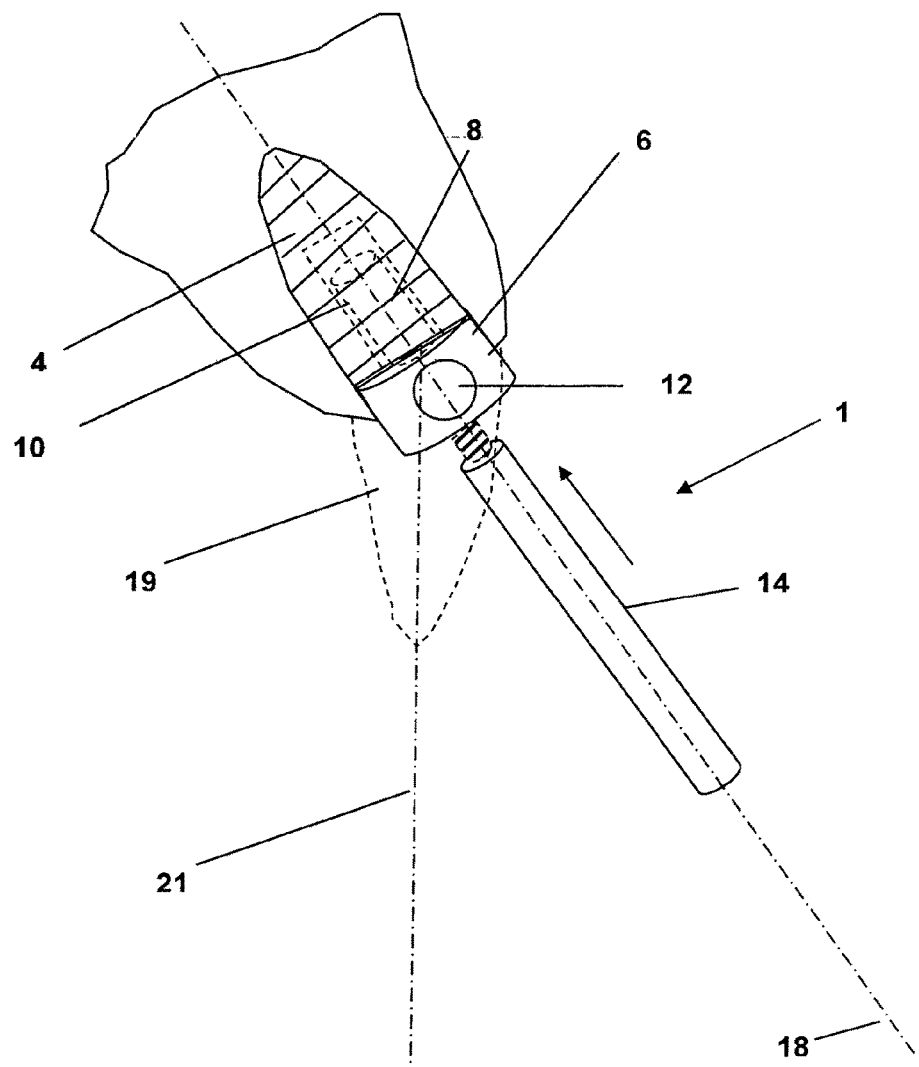
FIG. 2b shows the cross-sectional view of FIG. 2a after insertion of the conical projection into the internal hole of the dental implant.
Figure 2C:
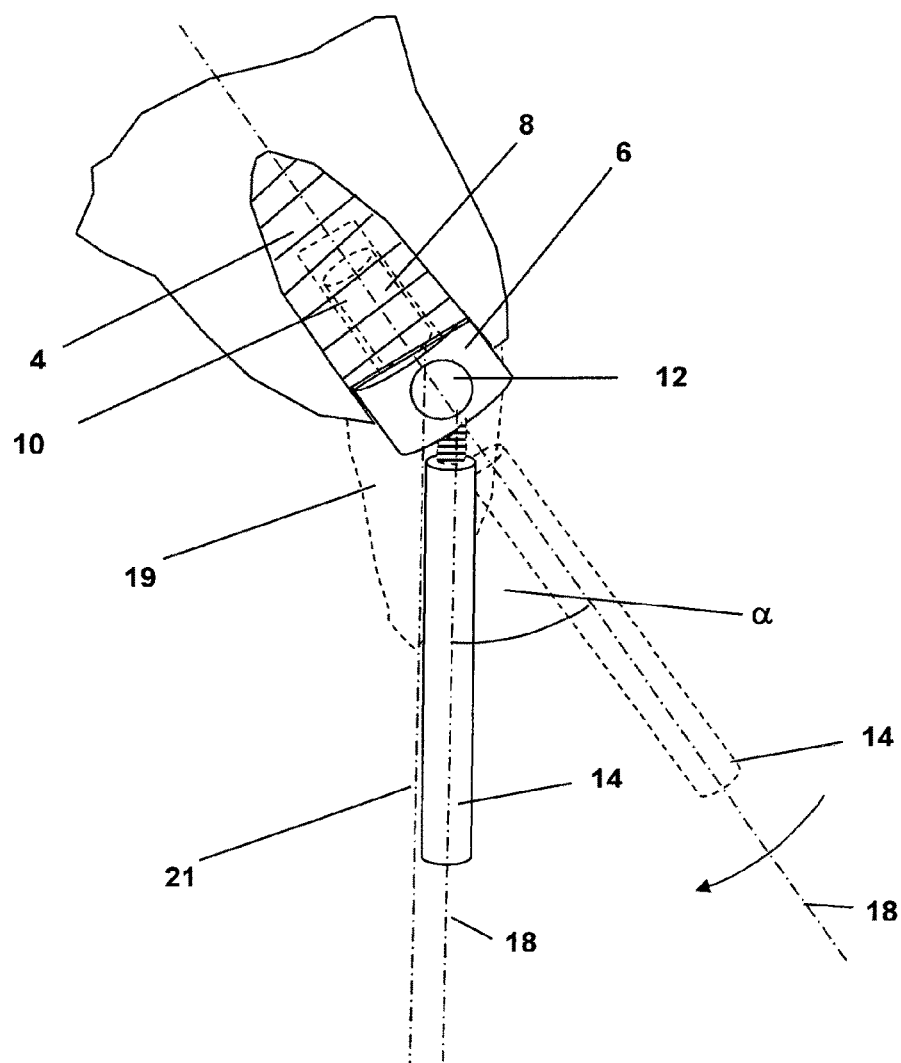
FIG. 2c shows the cross-sectional view of FIG. 2b after pivoting the rod-shaped indicator in a direction parallel to the longitudinal axis of an adjacent tooth.
Figure 2D:
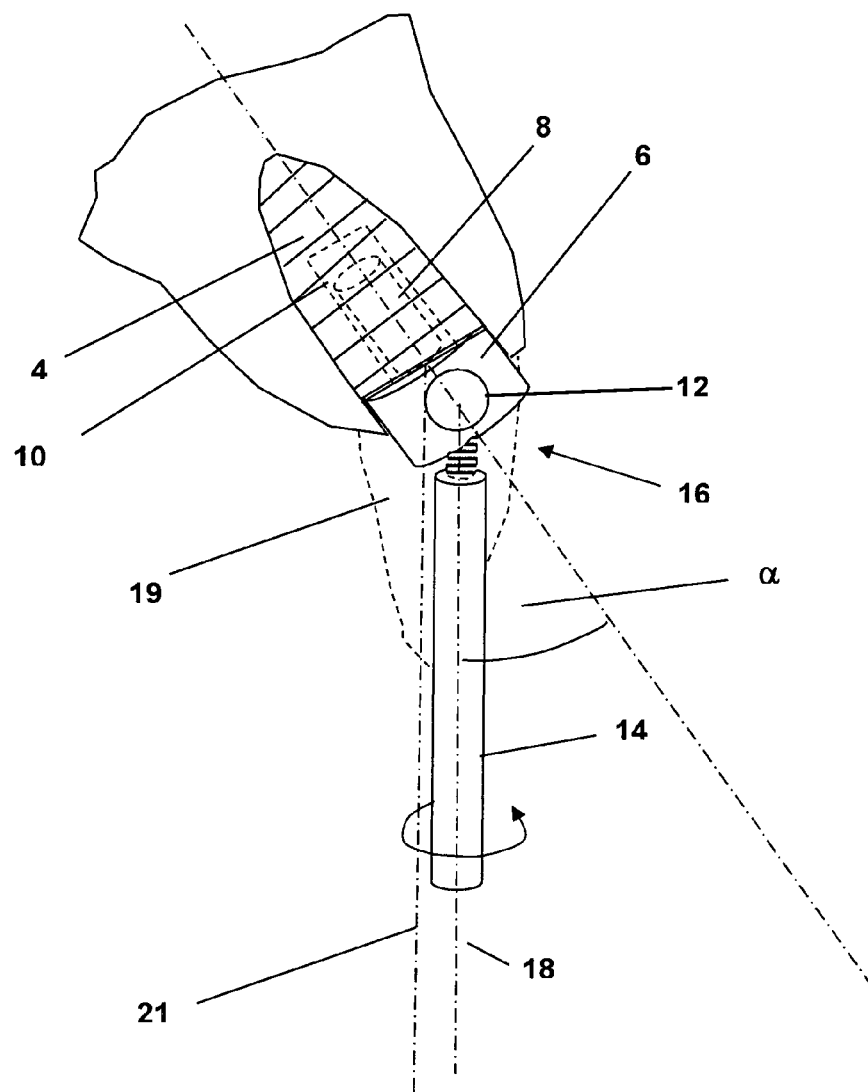
FIG. 2d shows the cross-sectional view of FIG. 2c during the rotation of the rod-shaped indicator to lock the indicator vis-à-vis the housing.
Figure 2E:
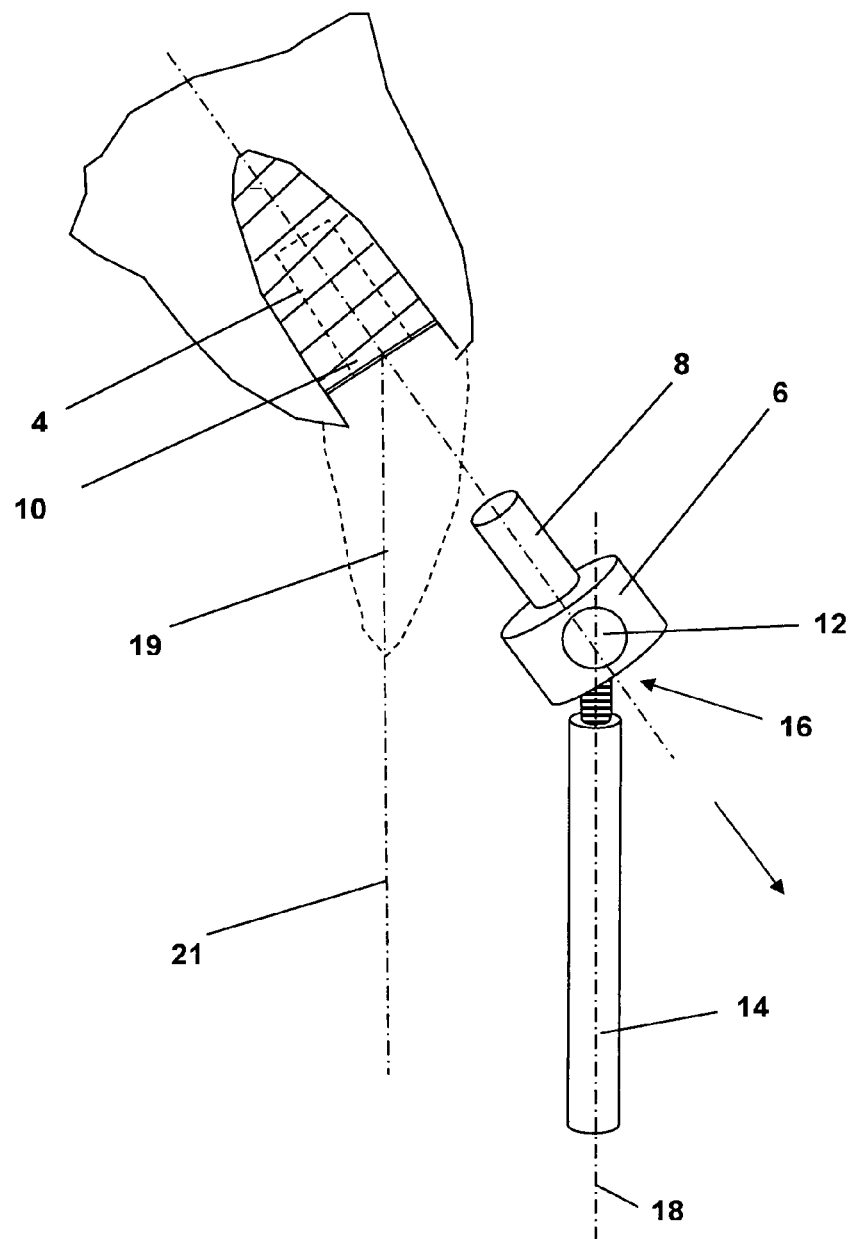
FIG. 2e shows the cross-sectional view from FIG. 2d after removing the device having a locked indicator.
Figure 3:
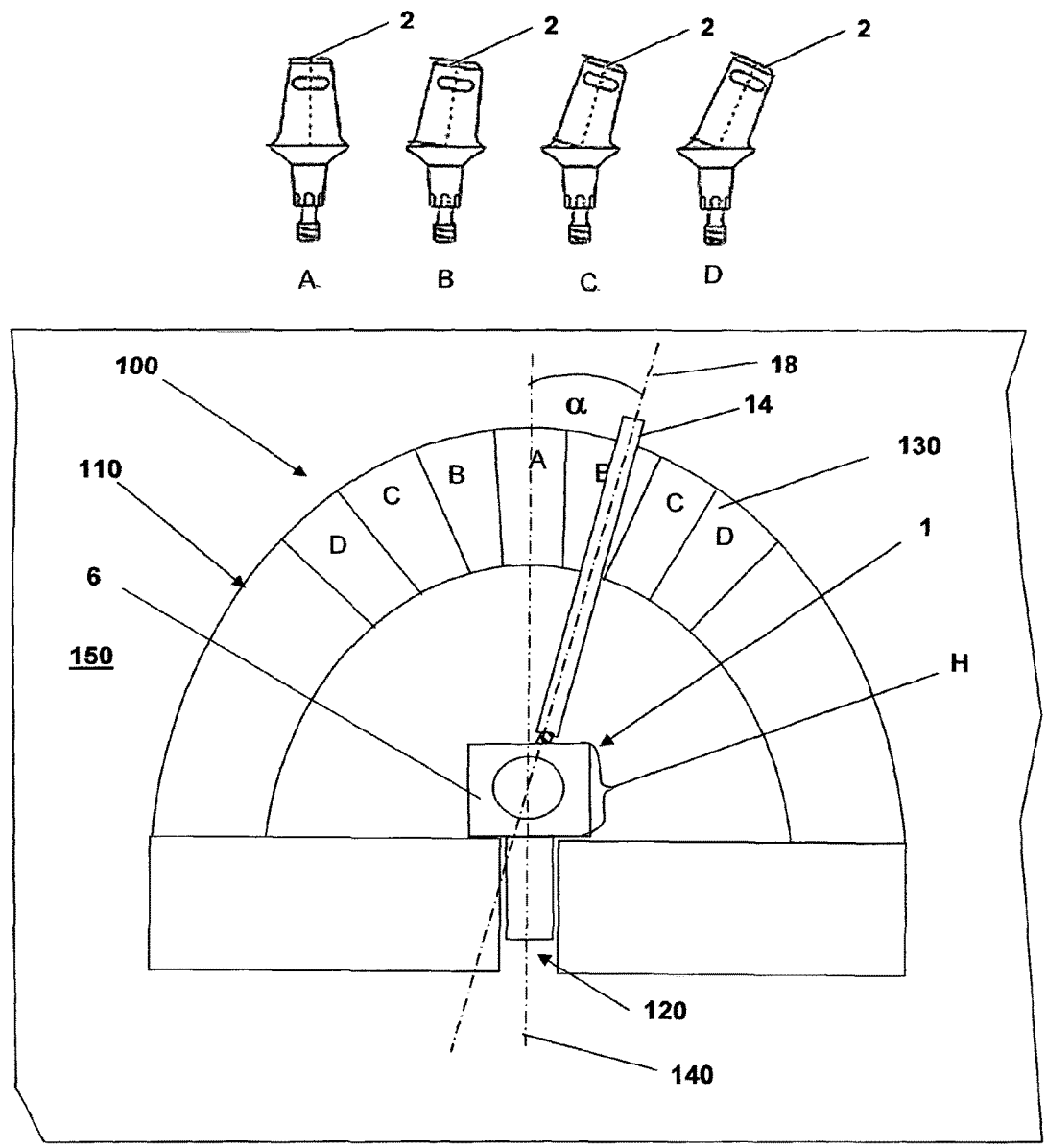
FIG. 3 shows an assembly according to the present disclosure for the selection of an angled abutment, in which the device according to the present disclosure having a locked indicator is inserted into a receiving opening of an indicator device.

As shown in FIG. 1a, according to the present disclosure, a device 1 for determining the angulation of an abutment shown in an exemplary manner in FIG. 3 or for a component 2 for a dental implant 4 includes a housing 6, at the exterior of which a conical projection 8 is formed. Conical projection 8 has such a diameter and such a length that it is insertable substantially without play into an internal hole 10 of dental implant 4 shown in an exemplary manner in FIGS. 2a through 2d, which previously has been inserted into the jaw bone of a patient.

As can be concluded in detail from the illustration of FIG. 1a and FIG. 1b, a rotary body 12 is rotatably accommodated in housing 6, at which a rod-shaped indicator 14 is disposed. Rotary body 12, which preferably from a position which is flushly aligned with conical projection 8, as it is shown in FIG. 2a, can be pivoted about an angle α, for example, of up to 45 degrees into an angled position shown in FIG. 2c, is in different rotational angle positions coupleable in a rotationally fixed manner to housing 6 by a locking device 16 acting between housing 6 and rotary body 12.

Figure 4A:
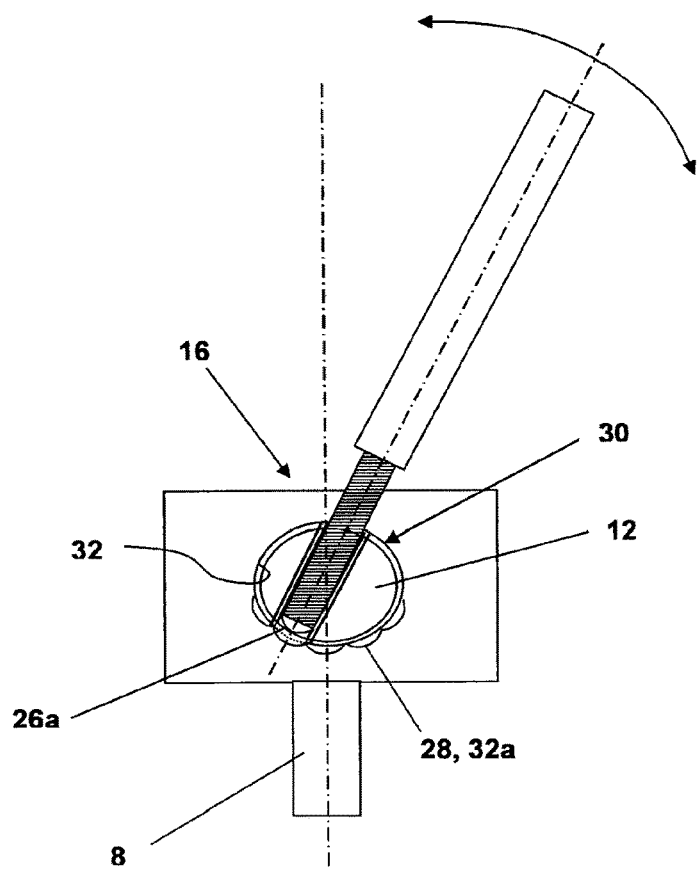
FIG. 4a shows schematically a cross-sectional view of a further embodiment having an indicator positionable in discrete angle positions in the released position.
Figure 4B:
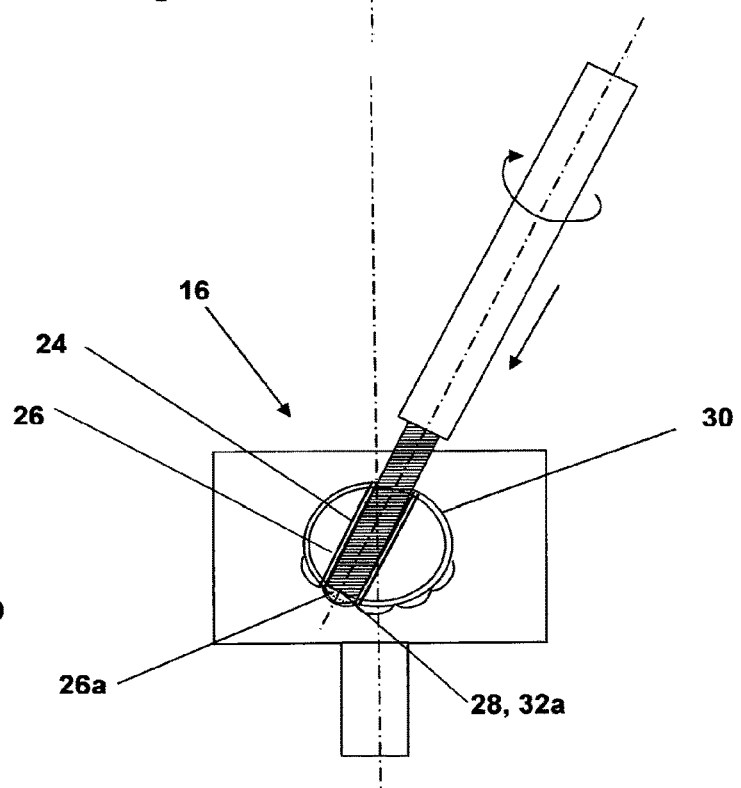
FIG. 4b shows the embodiment of FIG. 4a, in which the rod-shaped indicator is in the locked position.

In the preferred embodiment of the present disclosure, rotary body 12 is designed as a preferably cylindrical rotary body, which is accommodated in opening 20 of housing 6, which extends orthogonally to longitudinal axis 18 of rod-shaped indicator 14, as it is indicated in FIGS. 1a and 1b as well as also in FIGS. 4a and 4b.

In order to, on the one hand, be able to freely rotate rotary body 12, which is, in a similar manner as housing 6 and indicator 14, preferably made from metal, for example from stainless steel or also from plastic material, within opening 20, and, on the other hand, after reaching a desired rotational angle position, to precisely lock the rotary body in this position using only one hand, locking device 16 includes a through hole 22 formed in rotary body 12.

This through hole 22 is provided with an internal threaded section 24, into which an external thread 26 of rod-shaped indicator 14 can be screwed. In this instance, the length of threaded sections 24 and 26 is dimensioned in such a manner that, upon reaching a screw-locking position of indicator 14 shown in FIGS. 1b and 4b, end face 26a of the external threaded section 26 abuts against clamping surface 28 disposed in housing 6 and clamps rotary body 12 vis-à-vis housing 6.

This configuration of the present disclosure advantageously results in that the locking of rotary body 12 vis-à-vis housing 6 may be carried out by rotating rod-shaped indicator 14 manually or using a suitable instrument, in a very precise manner in a short period of time. As a result, the stress for the patient may advantageously also be kept to a minimum.

On the other hand, the previously described configuration of locking device 16 advantageously results in that, by the interaction of threaded sections 24 and 26, which preferably are fine thread sections, a very high clamping force may still be achieved using little effort, which ensures that rod-shaped indicator 14, when pulled out of the dental implant 4 and inserted into an indicator device 110, as it is shown in FIG. 3, subsequently still to be described in greater detail, does not accidentally twist.

In so doing, an unintentional adjustment of determined angle value α is advantageously prevented, which otherwise easily could lead to the selection of an abutment 2, the angulation angle of which does not come closest to the actual angle relationships between the longitudinal axis of dental implant 4 and longitudinal axis 21 extending through the adjacent teeth and/or dental implants 19. The same applies respectively to an angled abutment to be inserted, which serves as a basis for fastening a prosthesis for restoring the chewing function.

According to a further embodiment of the present disclosure, housing 6 has longitudinal slit-like opening 34 extending transversely to the rotary axis of rotary body 12, as this is shown in FIGS. 1a and 1b. Rod-shaped indicator 14 fastened to rotary body 12 extends through this opening 34 out of the interior of housing 6, as this is indicated in FIGS. 1a and 1b.

It advantageously results from this embodiment of housing 6 that the external threaded section 26 of indicator 14 by few hand movements can be screwed through longitudinal slit-like opening 34 in housing 6 into internal threaded hole 24 in rotary body 12. In so doing, device 1 may be assembled in little time from merely 3 components—housing 6, rotary body 12 and indicator 14—into a unit, which respectively can also be easily disassembled to clean or sterilize these components.

In the preferred embodiment of the present disclosure, opening 20 for rotary body 12 is, as it is shown in FIGS. 1a and 1b, a cylindrical bore 30, preferably configured as a blind hole, which is laterally introduced into housing 6.

In this embodiment of the present disclosure, a subregion of the cylindrical inner circumferential surface 32 of hole 30 forms clamping surface 28, at which end face 26a of external threaded section 26 of rod-shaped indicator 14 abuts if the indicator has been screwed in until the screw-locking position has been reached, as this is shown in FIGS. 1a and 1b.

On account of the inner circumferential surface of cylindrical hole 30 configured as cylindrical inner circumferential surface 32, in this instance, it advantageously results that, owing to locking device 16, rotary body 12 can be positioned in any angle position of a predefined rotation angle range, for example 0 through 45 degrees.

A further advantage resulting from this embodiment of the present disclosure, can be seen in that the positionability and lockability of rotary body 12 in any rotary angle position opens up the possibility to manufacture individual abutments 2, the angulation of which exactly corresponds with the angle between the longitudinal axis of dental implant 4 and longitudinal axis 21 of the adjacent teeth/superstructures 19.

According to a further idea based on the present disclosure, owing to locking device 16, rotary body 12 can, according to an embodiment of the present disclosure shown in FIGS. 4a and 4b, be positioned exclusively in predefined discrete angle positions.

By predefining discrete angle positions, which preferably correspond to the respective angulation angles of abutment 2 provided for a respective dental implant 4, it advantageously results that the type of abutment is automatically concretely indicated on the display device—as shown in FIG. 3—for the dentist.

This can, for example, occur with the aid of imprinted letters or other symbols or numbers, etc., which significantly facilitates the selection of the ideal abutment in practice and shortens the time required for such a selection.

In order to provide the predefined angle positions in which rotary body 12 is exclusively lockable by locking device 16, opening 20 for rotary body 12 has a hole introduced into housing 6, the inner circumferential surface 32 of which is, in the associated subregion forming clamping surface 28, provided with recesses 32a adjacent to one another, as it is shown in FIG. 4a and FIG. 4b.

The end of rod-shaped indicator 14 submerges into these recesses 32a. In this case, end face 26a of this end of the indicator is configured as a surface of external threaded section 26, which tapers in the fashion of a cone or a spherical surface in the direction of its center of recess 32a.

By respectively selecting the incline and the shape of the incline of recesses 32a adjacent to one another and of the angle or radius of end face 26a, in this instance, it can be advantageously achieved that end face 26a is always precisely aligned in the direction of the center of a recess 32a and, as a result, necessarily twists the rotary angle position of rotary body 12 if rod-shaped indicator 14 is increasingly further screwed into the screw-locking position.

According to a further idea based on the present disclosure, conical projection 8 is releasably connected to housing 6 and configured in such a manner that conical projections 8 can be fastened to housing 6 by different cross-sectional geometries and/or external geometries and/or diameters and/or lengths.

In so doing, it advantageously results that device 1 according to the present disclosure can be also inserted into dental implants of different manufacturers in that the conical projection is adapted to the shape and the diameter of the internal hole of the respective implant.

For this purpose, it may, for example, be provided that the conical projection has a pin having a small diameter, which is fastened to the housing and onto which a sleeve having an internal hole corresponding to the diameter of the pin is slid, the outer diameter of which corresponding to the shape of the internal hole of implant 1. In this instance, the pin and the sleeve may have a polygonal or also oval cross-sectional shape to secure the sleeve against a twisting vis-à-vis the housing.

In the previous embodiments, internal hole 10 is also to be understood as an opening introduced into the implant body, which retroactively has been milled and which has one or a plurality of known indexing elements, by which the abutment can be inserted in a predefined alignment.

In the same manner, the opening in implant body 4 can, for example, feature a polygonal, in particular hexagonal, socket or another geometric toothing, which may be provided for the insertion of a screw implant and/or for a subsequently defined alignment and/or rotational securing of an abutment.

The method steps for using device 1 according to the present disclosure are subsequently described on the basis of FIGS. 2a through 2e.

As it is shown in FIGS. 2a and 2b, device 1 is, by rod-shaped indicator 14 flushly aligned with internal hole 10, inserted leading with conical projection 8 into internal hole 10 of a previously implanted dental implant 4, and indicator 14 may be in the released position or also in the locked position.

Subsequently, rod-shaped indicator 14 is, locking device 16 being unlocked, pivoted about a pivot angle α until longitudinal axis 18 of indicator 14—as shown in FIG. 2c—is aligned in a parallel manner to longitudinal axis 21 of an adjacent tooth or a superstructure 19 and/or a desired alignment of a prosthesis for restoring the chewing function. In this position, locking device 16 is then, by rotating rod-shaped indicator 14 in the clockwise direction, locked or closed, as this is indicated by the arrow not referenced in greater detail in FIG. 2d.

As a result, housing 6 is coupled in a rotationally fixed manner to rotary body 12, to which rod-shaped indicator 14 in turn is fastened, which in the selected rotary angle position is accordingly fixed relative to housing 6.

Next, device 1 according to the present disclosure is again removed from dental implant 4 and, leading by conical projection 8, inserted into a receiving opening 120 of an indicator device 110 shown in FIG. 3. Indicator device 110 has an indicator scale 130 laterally disposed at receiving opening 120, which extends in a plane 150 running parallel to longitudinal axis 140 of receiving hole 120. On indicator scale 130, symbols or numbers are disposed, which in an exemplary manner are listed as letters A, B, C, D in FIG. 3. The letters are disposed in respective sectors which span the angular area about the angulation angle of an assigned abutment of a plurality of abutments, which in the illustration of FIG. 3 are symbolically disposed above indicator scale 130 and are denoted by the same letters A, B, C or D.

This configuration of the present disclosure enables the dentist to select, on the basis of angle α adjusted between rod-shaped indicator 14 and conical projection 8, the associated abutment, in this case the abutment with the reference character B, from the plurality of the predefined abutments A, B, C, D, without, for example, previously measuring the angle by a measuring device and without having to manually determine at great effort the associated abutment by an angulation angle which comes closest.

Assembly 100, formed in the previously described manner, for selecting an angled abutment 2 for an implanted dental implant 4 from a plurality of predefined abutments having different angulation angles, which, on the one hand, includes device 1 and, on the other hand, indicator device 110, enables to advantageously widely prevent errors when selecting an abutment having the most suitable angulation, and to minimize the required time and the stress on the patient for the selection of most suitable abutment 2.

In this instance, in order to simultaneously also being able to consider different heights and shapes of the gingiva surrounding inserted implant 2, it may be furthermore provided to provide two or a plurality of groups of devices 1 according to the present disclosure, in which housing 6 of each group has a uniform outer basic form corresponding respectively to the gingival shape of abutment 2 and in which housings 6 in each group merely differ in their heights H. In this way, for example four housing heights H may be provided for each housing shape/gingival shape, which correspond to respective abutments 2 having a gingival height of, for example, 0.5 mm, 0.75 mm, 1.5 mm and 2 mm.

According to a further idea based on the present disclosure, the angulation angle read out from indicator scale 130 or determined in any other manner may be used to manufacture, for example produced with the aid of CAD/CAM technology, an abutment 2 individual to a patient.

What is claimed is:

1. An assembly for selecting one of a plurality of predefined abutments having different angulation angles, the assembly comprising:
   a device for determining an abutment angulation for a dental implant, the device comprising:
      a housing,
      a projection fastened to the outside of the housing, which is insertable into an internal hole of the dental implant,
      a rotary body rotatable in the housing relative to the projection,
      a rod-shaped indicator connected to the rotary body and extending away therefrom such that a majority of a length of the rod-shaped indicator is disposed outside the housing, and
      a locking device for releasably coupling the rotary body to the housing, wherein the rotary body is rotatable to allow the rod-shaped indicator to pivot among a plurality of different angular positions relative to the projection, wherein each of the plurality of different angular positions of the rod-shaped indicator is determined by the angle between a longitudinal axis of the rod-shaped indicator and a longitudinal axis of the projection, and wherein the rod-shaped indicator may be locked in any one of the plurality of different angular positions by the locking device coupling the rotary body to the housing;
   an indicator device, which comprises a receiving opening for accommodating the projection of the device, the receiving opening having a longitudinal axis, and
   a display scale disposed laterally from the receiving opening and extending in a plane disposed parallel to the longitudinal axis of the receiving opening, wherein an angle between the longitudinal axis of the receiving opening and the longitudinal axis of the rod-shaped indicator can be read from the display scale, the angle read from the display scale being usable to select the one of the plurality of predefined abutments.

2. The assembly as recited in claim 1, wherein the rotary body is rotationally accommodated in an opening of the housing extending orthogonally to the longitudinal axis of the rod-shaped indicator.

3. The assembly as recited in claim 2, wherein the locking device includes a through hole formed in the rotary body, the through hole having an internal threaded section, into which an external threaded section of the rod-shaped indicator is screwable in such a manner that an end face of the external threaded section, upon reaching a screw-locking position of the rod-shaped indicator, abuts a clamping surface in the housing and clamps the rotary body to the housing.

4. The assembly as recited in claim 3, wherein the plurality of different angular positions of the rod-shaped indicator correspond to angle positions of the rotary body relative to the projection, wherein each of the angle positions of the rotary body is determined by the angle between a longitudinal axis of the through hole and the longitudinal axis of the projection.

5. The assembly as recited in claim 4, wherein the rotary body may be selectively coupled to the housing by the locking device to lock the rotary body in one of the angle positions relative to the projection, and wherein the angle positions are predetermined.

6. The assembly as recited in claim 5, wherein the opening in the housing for accommodating the rotary body is a cylindrical hole in the housing, wherein a subregion of an inner circumferential surface of the cylindrical hole forms the clamping surface, and wherein the subregion of the inner circumferential surface is provided with recesses adjacent to one another, wherein the recesses correspond to the angle positions, respectively, such that when the rotary body is in a particular one of the angle positions and the rod-shaped indicator is in the screw-locking position, the end face of the external threaded section is disposed in the recess corresponding to the particular one of the angle positions.

7. The assembly as recited in claim 3, wherein the opening in the housing for accommodating the rotary body is a cylindrical blind hole, and wherein the clamping surface is a subregion of a cylindrical inner circumferential surface of the cylindrical blind hole.

8. The assembly as recited in claim 1, wherein the projection is releasably connected to the housing.

9. The assembly as recited in claim 1, wherein the housing has a slit-like opening extending transversely to a rotary axis of the rotary body, through which the rod-shaped indicator, which is fastened to the rotary body, extends from an interior of the housing.

10. The assembly as recited in claim 1, wherein the housing has a height corresponding to the gingival height of the abutment.

11. An assembly for selecting one of a plurality of predefined abutments having different angulation angles, the assembly comprising:
   a device for determining an abutment angulation for a dental implant, the device comprising:
      a housing,
      a projection fastened to the outside of the housing, which is insertable into an internal hole of the dental implant,
      a rotary body rotatable in the housing relative to the projection,
      a rod-shaped indicator connected to the rotary body and extending away therefrom such that a majority of a length of the rod-shaped indicator is disposed outside the housing, and
      a locking device for releasably coupling the rotary body to the housing,
      wherein the rotary body is rotatable to allow the rod-shaped indicator to pivot among a plurality of different angular positions relative to the projection, wherein each of the plurality of different angular positions of the rod-shaped indicator is determined by the angle between a longitudinal axis of the rod-shaped indicator and a longitudinal axis of the projection, and wherein the rod-shaped indicator may be locked in any one of the plurality of different angular positions by the locking device coupling the rotary body to the housing;
   an indicator device, which comprises a receiving opening for accommodating the projection of the device, the receiving opening having a longitudinal axis, and
   a display scale disposed laterally from the receiving opening and extending in a plane disposed parallel to the longitudinal axis of the receiving opening, the display scale including a plurality of marked sectors corresponding to the plurality of predefined abutments, respectively, and wherein the location of the rod-shaped indicator relative to the marked sectors indicates the one of the plurality of predefined abutments that should be selected.

12. The assembly as recited in claim 11, wherein the rotary body is rotationally accommodated in an opening of the housing extending orthogonally to the longitudinal axis of the rod-shaped indicator.

13. The assembly as recited in claim 12, wherein the locking device includes a through hole formed in the rotary body, the through hole having an internal threaded section, into which an external threaded section of the rod-shaped indicator is screwable in such a manner that an end face of the external threaded section, upon reaching a screw-locking position of the rod-shaped indicator, abuts a clamping surface in the housing and clamps the rotary body to the housing.

14. The assembly as recited in claim 13, wherein the plurality of different angular positions of the rod-shaped indicator correspond to plurality of different angle positions of the rotary body relative to the projection, wherein each of the angle positions of the rotary body is determined by the angle between a longitudinal axis of the through hole and the longitudinal axis of the projection.

15. The assembly as recited in claim 14, wherein the rotary body may be selectively coupled to the housing by the locking device to lock the rotary body in one of the angle positions relative to the projection, and wherein the angle positions are predetermined.

16. The assembly as recited in claim 15, wherein the opening in the housing for accommodating the rotary body is a cylindrical hole in the housing, wherein a subregion of an inner circumferential surface of the cylindrical hole forms the clamping surface, and wherein the subregion of the inner circumferential surface is provided with recesses adjacent to one another, wherein the recesses correspond tote angle positions, respectively, such that when the rotary body is in a particular one of the angle positions and the rod-shaped indicator is in the screw-locking position, the end face of the external threaded section is disposed in the recess corresponding to the particular one of the angle positions.

17. The assembly as recited in claim 13, wherein the opening in the housing for accommodating the rotary body is a cylindrical blind hole, and wherein the clamping surface is a subregion of a cylindrical inner circumferential surface of the cylindrical blind hole.

18. The assembly as recited in claim 11, wherein the projection is releasably connected to the housing.

19. The assembly as recited in claim 11, wherein the housing has a slit-like opening extending transversely to a rotary axis of the rotary body, through which the rod-shaped indicator, which is fastened to the rotary body, extends from an interior of the housing.

* * * * *

UNITED STATES PATENT AND TRADEMARK OFFICE
CERTIFICATE OF CORRECTION

PATENT NO. : 10,441,388 B2
APPLICATION NO. : 15/753329
DATED : October 15, 2019
INVENTOR(S) : Volker Biehl Page 1 of 1

It is certified that error appears in the above-identified patent and that said Letters Patent is hereby corrected as shown below:

In the Claims

Column 10, Line 35, Claim 16 delete "tote" and insert therefor: --to the--

Signed and Sealed this
Thirteenth Day of October, 2020

Andrei Iancu
*Director of the United States Patent and Trademark Office*